United States Patent [19]

Shikani

[11] Patent Number: 5,246,455
[45] Date of Patent: Sep. 21, 1993

[54] MIDDLE MEATAL ANTROSTOMY VENTILATION TUBE

[75] Inventor: Alain H. Shikani, Baltimore, Md.

[73] Assignee: Micromedics, Inc., Eagan, Minn.

[21] Appl. No.: 702,585

[22] Filed: May 17, 1991

[51] Int. Cl.⁵ .............................................. A61F 2/18
[52] U.S. Cl. ......................................... 623/10; 623/11
[58] Field of Search ................... 623/10, 11, 15, 9; 606/109, 153, 196, 232

[56] References Cited

U.S. PATENT DOCUMENTS

| | | | |
|---|---|---|---|
| 4,031,569 | 6/1977 | Jacob | 128/1 R |
| 4,094,303 | 6/1978 | Johnston | 128/1 R |
| 4,274,162 | 6/1981 | Joy et al. | 606/109 |
| 4,534,761 | 8/1985 | Raible | 604/175 |
| 4,650,488 | 3/1987 | Bays | 623/12 |
| 4,704,126 | 11/1987 | Baswell | 623/10 |
| 4,744,792 | 5/1988 | Sander | 623/10 |
| 5,053,040 | 10/1991 | Goldsmith, III | 606/109 |

FOREIGN PATENT DOCUMENTS 8706817  11/1987  World Int. Prop. O. ............ 623/9

Primary Examiner—David Isabella
Assistant Examiner—Debra S. Brittingham
Attorney, Agent, or Firm—Haugen and Nikolai

[57] ABSTRACT

An implantable ventilation tube for insertion in bodily tissues is disclosed. A suggested use for such a tube is as a middle meatal antrostomy ventilation tube for use following endoscopic surgery. It consists of a pair of flanges and a central tubular vent section extending therebetween, having the flanges positioned perpendicular to the lumen of the central tubular vent section. The tube is preferably made of elastomeric material and may include grooves etched in the distal surface of the distal flange to assist in insertion by permitting materials of a higher durometer rating than silastic ® to be folded then grasped during insertion. It is suggested that the proximal flange be generally rectangular shaped, while the distal flange be generally triangular shaped, to ease insertion yet enhance anchoring capabilities. Once properly positioned through an opening prepared in a body cavity or duct, the ventilation tube permits the unhindered flow of fluids, such as air, through the lumen.

3 Claims, 2 Drawing Sheets

MIDDLE MEATAL ANTROSTOMY VENTILATION TUBE

BACKGROUND OF THE INVENTION

I. Field of the Invention

This invention relates generally to the design of ventilation tubes for medical applications and more particularly to a ventilation tube for placement in the region of the nasal sinuses following endoscopic antrostomy. The presence of the tube retards scarring and adhesion; thus, it promotes healing and lessens post-operative complications.

Functional endoscopic sinus surgery, or antrostomy, is becoming increasingly popular in the treatment of chronic nasal and paranasal sinus disease. Following such surgery, the middle turbinate, a structure within the nasal cavity, has a tendency to move laterally towards the lateral nasal wall. During an irritated, post-surgical state, this movement promotes synechiae (adhesion) formation, whereby normally freely hanging structures become physically adhered to other structures adjacent to the sinuses. This can subsequently result in increased susceptibility to renewed infection of the osteomeatal complex. Obstruction can also occur, as the tissues become increasingly adhered to one another.

To prevent lateral movement of the middle turbinate and reduce the possibility of such synechiae formation, a stent can be placed between the middle turbinate and the lateral nasal wall to hold them apart until sufficient healing has occurred in the area that the conditions which promote synechiae formation have subsided. Thus, the presence of the stent will prevent adhesion or synechiae formation. The stent will also function as a ventilation tube that will maintain the patency of the middle meatal antrostomy and promote aeration and drainage of the sinuses. The use of a post-operative stent also furthers the goals of the surgery to restore mucociliary clearance and prevent osteopathology.

II. Discussion of the Prior Art

An externalizing shunt disclosed in U.S. Pat. No. 4,534,761 to Raible. It consists of an unobstructed passageway having an annular rim and an anchor of grafting mesh positioned midway along the outer circumference of the device. It is formed from either pyrolytic or vitreous carbon over a graphite substrate. The exterior surfaces, including the grafting mesh, are coated with collagen in order to enhance adhesion to the surrounding tissues. There is no indication of the dimensions of the device, but the anchor includes a plurality of apertures that essentially span the width of the anchor and receive suture material or otherwise stabilize the device.

Shunts are commonly used in other medical applications. They are commonly used to ventilate the inner regions of the ear. Such ear tubes are shown in U.S. Pat. Nos. 4,744,792, 4,704,126 and 4,650,488. The U.S. Pat. No. '792 patent to Sander, et al. discloses a fluoroplastic polymer coated titanium or titanium alloy ventilation tube with spaced apart flanges. The flange that will be adjacent the outer ear canal may have a plurality of radially spaced openings which facilitate insertion by providing sites that may be grasped by a forceps. An optional bore liner is provided to promote the ingrowth and adhesion of tissue. The U.S. Pat. No. '126 patent to Baswell discloses a similar titanium or titanium alloy ear tube implant. Rather than having a biocompatible fluoroplastic coating, the exterior surfaces of the Baswell U.S. Pat. No. '126 device are polished to a smooth, matte finish.

U.S. Pat. No. 4,650,488 to Bays, et al. discloses an implant made of a biodegradable material. It is dimensioned for implantation between the middle and inner ear. To aid in insertion, one region of the outer flange has a tab which extends perpendicular to the surface of the tympanic membrane and can be grasped with a forceps, hemostat or similar device.

The shunts disclosed in the U.S. Pat. No. '792, '126 and '488 patents are all composed of inflexible or brittle materials that are not well suited to bending or, if bent, lack a memory capacity to return them to their original configuration. Due to a desire to minimize the degree of invasion into nasal tissue, it is desirable to utilize an elastomeric material that can be coaxed into proper position using a slit in the tissues having minimal dimensions. A flexible elastomer is also thought to be less traumatic, producing less abrasion of surrounding tissues during and after insertion.

It is accordingly a principal object of the present invention to provide a new and improved ventilation tube that will physically separate structures within the sinuses and thus promote post-surgical recovery.

Another object is to provide a ventilation tube for us in antrostomy procedures to enhance aeration and drainage of the post-surgical region.

Yet another object is to provide a middle meatal ventilation tube that will mechanically separate the middle turbinate and the lateral nasal wall during the post-surgical recovery period and thus prevent the formation of synechiae and other adhesions.

A further object is to provide a middle meatal ventilation tube that is composed of relatively atraumatic elastomeric material in order to minimize tissue damage.

Another principal object of the invention is to provide a method for properly inserting the ventilation tube.

SUMMARY OF THE INVENTION

The foregoing objects and advantages of the invention are achieved by providing a ventilation tube for use following procedures such as middle meatal antrostomy, having a pair of flanges mounted at opposing ends of the tube. In the preferred embodiment, one flange has a triangular shape and the other flange has an elongated rectangular shape, preferably rounded at the free ends.

In profile, the ventilation tube of the preferred embodiment is generally H-shaped, with the triangular flange having a shorter longitudinal axis than the other flange. The length of the bore of the tube is approximately one-sixth of the longitudinal axis of this triangular flange, and the length of the tube is approximately one-half of its diameter.

The ventilation tube is comprised of elastomeric material such as silicone or flexible polyurethanes. When less flexible materials of higher durometer rating are selected, grooves are positioned on the triangular flange near the exterior of the bore to assist in folding the flange during the insertion process.

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE PREFERRED EMBODIMENT

Figure 1:
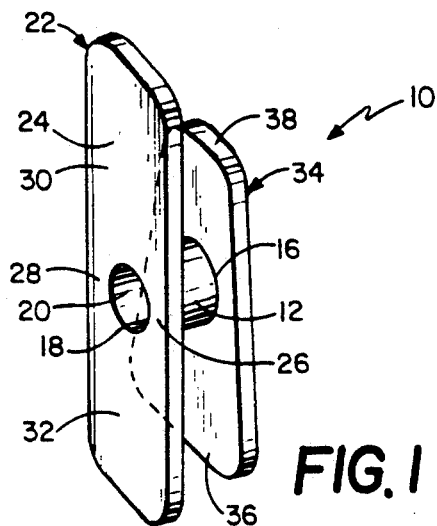
FIG. 1 is a perspective view of the ventilation tube in accordance with one embodiment of the present invention.

Referring to FIG. 1, there is indicated generally by numeral 10 a middle meatal antrostomy ventilation tube constructed in accordance with the present invention. The ventilation tube 10 is preferably molded from a suitable medical grade elastomeric material. Ventilation tube 10 includes a central tubular section 12. The central tubular section 12 has a proximal end 14 (shown in FIG. 2), a distal end 16, and a lumen 18 extending between the two ends. Both proximal 14 and distal 16 ends of the central tubular section 12 are open to form a bore 20 which permits fluid such as air to flow unimpeded through the central tubular section 12. Fitted onto the proximal end 14 of the tubular vent 12 is a generally elongated rectangular flange 22 having a flat planar surface 24, two short sides 26 and 28, and two long sides 30 and 32. The long sides 30 and 32 are proportioned in relation to the diameter of the central tubular section 12. The length of the two long sides 30 and 32 are each approximately three times the diameter of the bore 20 through the central tubular section 12.

Fitted onto the distal end 16 of the tubular vent 12 is a generally triangular flange 34 which is slightly shorter from its base 36 to its apex 38 than the combined length of the long sides 30 and 32 of the elongated rectangular flange 22. The triangular flange 34 is preferably centered about the lumen 18. As mentioned previously, lumen 18 extends through both the flanges 22 and 34 so that fluids, such as air, can pass through the ventilation tube 10.

Figure 2:
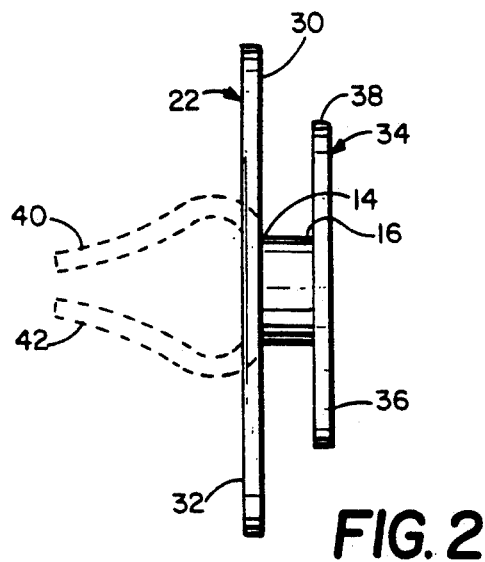
FIG. 2 is a cross-sectioned side view of the ventilatior tube of Figure 1.

As can best be seen in FIG. 2, the flanges 22, 34 form a generally H-shaped structure when attached to the central tubular section 12. Insertion of the ventilation tube 10 is performed by grasping the two long sides 30, 32 of the elongated rectangular flange 22 and folding them over until they lie in parallel relation 40, 42 to the side of the central tubular section 12, whereupon they may be securely grasped with a hemostat or forceps (not shown).

Figure 3:
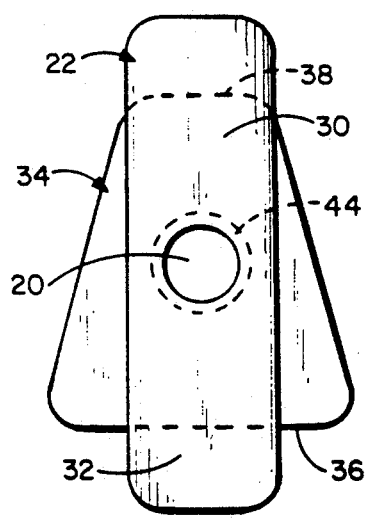
FIG. 3 is a proximal end view of the ventilation tube of FIG. 1.

FIG. 3 presents a proximal end view of the ventilation tube 10 in which the relative proportions of the components of the device can more clearly be seen. Dimensions and materials reported herein are exemplary only and not intended to be of any limiting value. It is suggested that the ventilation tube 10 be composed of a flexible, elastomeric material such as silicone or polyurethane. A suggested diameter for the bore 20 of the central tubular section 12 is in the range of 0.250–0.375 inch, having a wall thickness 44 dependent upon both the durometer rating of the elastomeric material used and the overall dimensions of the device. If medical grade silicone is selected, a suggested wall thickness would be in the range of 0.01–0.06 inch. A suggested range for the overall length of the two long sides 30, 32 of the elongated rectangular flange 22 is 1.35–1.5 inch, with the overall length of the triangular flange 34 from base 36 to apex 38 being slightly shorter than that of the rectangular flange 22 by an amount approximately equal to the diameter of the bore 20 of the central tubular section 12. The length of the base 36 of the triangular flange 34 is approximately equal to the distance from the base 36 to the apex 38.

Figure 4:
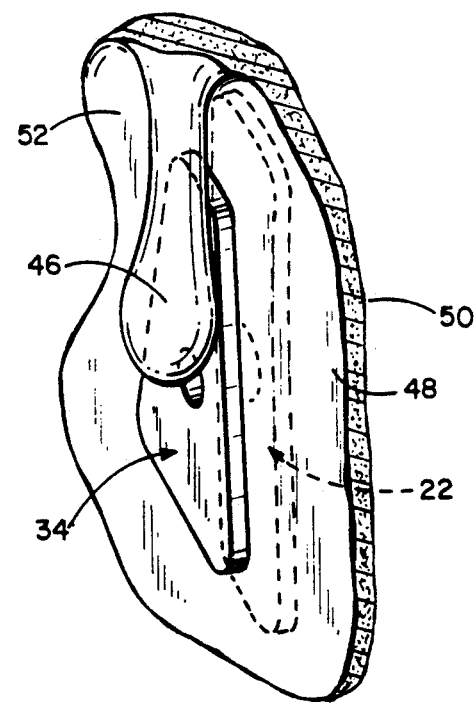
FIG. 4 is a view of the ventilation tube of FIG. 1 in situ.

The ventilation tube 10 of the present invention is depicted in situ in FIG. 4, wherein it is positioned between the middle turbinate 46 and the lateral nasal wall 48. The ventilation tube 10 is positioned by first securely grasping the long sides 30, 32 of the elongated rectangular flange 22 with a hemostat or forceps (as depicted in shadow in FIG. 2).

With the visual assistance of an endoscope (not shown), the hemostat or forceps can then be used to advance the ventilation tube 10 up the nasal passage 50 to a site where an antrostomy opening has been prepared in the lateral nasal wall. The triangular flange 34 is angularly urged through this antrostomy until fully inserted within the nasal sinus 52, whereupon it comes to rest against the lateral nasal wall 48 (i.e., the medial wall of the maxillary sinus), with the middle turbinate 46 free to bump against it. The elongated rectangular flange 22 rests upon the opposite surface of the medial wall of the maxillary sinus.

DESCRIPTION OF ALTERNATIVE EMBODIMENTS

Figure 5:
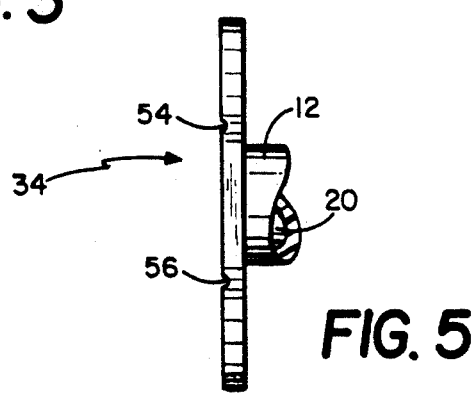
FIG. 5 is a cross-sectioned partial side view of an alternative embodiment of the present invention.
Figure 6:
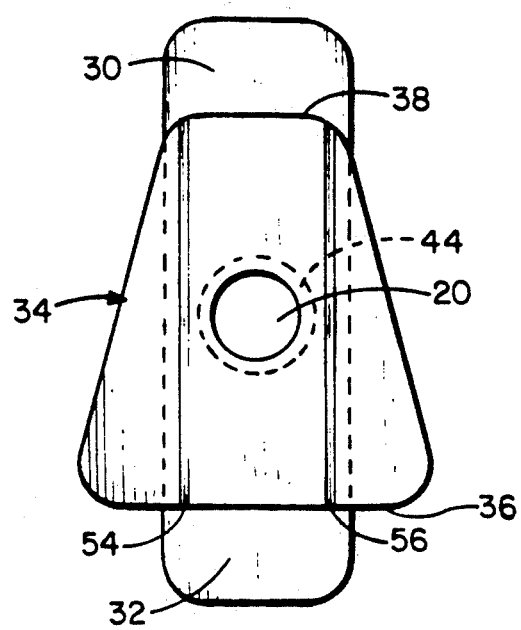
FIG. 6 is a distal end view of the ventilation tube of FIG. 1.

FIGS. 5 and 6 depict an alternative embodiment for the triangular flange 34. If it is desired to use a medical grade elastomeric material of higher durometer rating than silastic ®, flexation can become difficult. To ease insertion through the small nasal passage, it is sometimes advantageous to bend the corners of the triangular flange 34 so that they are flush with the central tubular section 12. If the ventilation tube 10 is made of a material of higher durometer rating than silastic ®, grooves 54 and 56 may be etched in the external flat planar surface of the triangular flange 34 near the bore 20 of the central tubular section 12 and parallel to the edges of the rectangular flange 22. It is suggested that the grooves 54, 56 be placed a distance from the bore 20 which does not exceed the diameter of the bore 20.

FIG. 6 more clearly depicts the positioning of the grooves 56 and 58 on the exterior surface of the triangular flange 34. To assist in bending materials of durometer rating higher than silastic ®, the grooves 56 and 58 extend the full length of the triangular flange 34, from base 36 to apex 38.

Figure 7:
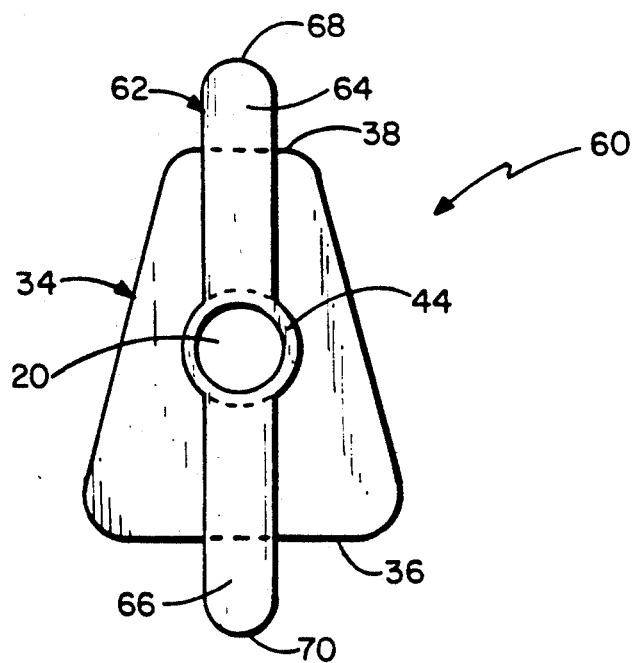
FIG. 7 shows an alternative embodiment of the present invention.

An alternative embodiment of the present invention featuring a more narrow profile is depicted in FIG. 7. Generally depicted as 60, this embodiment lacks the sides 26, 28 shown on the generally rectangular flange 22 of FIG. 1. Specifically, flange 62 features sides 64 and 66 having a length similar to the long sides 30, 32 in FIG. 1, but having rounded tips 68 and 70 and a width that is less than the diameter of the bore 20. Thus, the sides 64 and 66 are not contiguous and are supported by the wall 44 of the central tubular section 12. This configuration permits easier passage through narrow channels than can be accomplished with the embodiment of FIG. 1.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. An implantable stent for insertion into a lateral wall of a nasal cavity of a patient following functional endoscopic middle meatal antrostomy procedure for venting a maxillary sinus of said patient while establishing a barrier to the formation of adhesions and synechiae between said later wall and a middle turbinate of said patient, comprising:
    (a) a flexible, plastic, tubular vent member having first and second open ends and a lumen of a predetermined diameter extending therebetween, said vent member including
        (i) a first, generally rectangular, flexible flange member integrally formed on said first open end of said tubular vent member, said first flexible flange member having a width dimension approximately equal to said diameter of said lumen of said tubular vent member and said first flexible flange member having a length dimension from about five to six times said width dimension,
        (ii) a second, generally triangular, flexible flange member integrally formed on said second open end of said tubular vent member, said triangular flange member having height and base dimensions providing said triangular flange member with an area sufficient to effectively maintain separation between said lateral wall of said nasal cavity of said patient and said middle turbinate.

2. The implantable stent as in claim 1 wherein said stent comprises a one-piece, molded, silastic device.

3. The implantable stent as in claim 1 wherein said base dimension is about equal to said height dimension.

* * * * *

UNITED STATES PATENT AND TRADEMARK OFFICE
CERTIFICATE OF CORRECTION

PATENT NO. : 5,246,455

DATED : September 21, 1993

INVENTOR(S) : ALAIN H. SHIKANI

It is certified that error appears in the above-identified patent and that said Letters Patent is hereby corrected as shown below:

Col. 5, line 21, delete "later", insert --lateral--

Signed and Sealed this

Twenty-ninth Day of March, 1994

*Attest:*

BRUCE LEHMAN

*Attesting Officer*  *Commissioner of Patents and Trademarks*